United States Patent [19]

Ojima

[11] Patent Number: 4,969,913
[45] Date of Patent: Nov. 13, 1990

[54] CERAMICS COMPOSITES
[75] Inventor: Satoshi Ojima, Tokyo, Japan
[73] Assignee: Asahi Kogaku Kogyo K.K., Tokyo, Japan
[21] Appl. No.: 249,690
[22] Filed: Sep. 27, 1988
[30] Foreign Application Priority Data Sep. 28, 1987 [JP] Japan .................. 62-243511

[51] Int. Cl.$^5$ ............ A61F 2/00; A61F 2/28
[52] U.S. Cl. .................... 623/66; 623/16; 433/202.1; 433/212.1
[58] Field of Search ........... 623/16, 66; 433/201.1, 433/202.1, 212.1, 222.1, 223; 501/1, 80

[56] References Cited

U.S. PATENT DOCUMENTS

| | | |
|---|---|---|
| 3,505,158 | 4/1970 | Murray . |
| 4,113,500 | 9/1978 | Ebihara et al. . |
| 4,149,894 | 4/1979 | Ebihara et al. . |
| 4,230,455 | 10/1980 | Hidaka et al. . |
| 4,237,559 | 12/1980 | Borom .................. 623/16 |
| 4,447,210 | 5/1984 | Hidaka et al. . |

FOREIGN PATENT DOCUMENTS

| | | |
|---|---|---|
| 51116809 | 5/1950 | Japan . |
| 52-4515 | 1/1977 | Japan . |
| 58-41854 | 9/1983 | Japan . |
| 62-14846 | 1/1987 | Japan . |

OTHER PUBLICATIONS

A Copy of U.K. Search Report of U.K. Appln. No. 88227541.
English Translation of Claim 1 of JP No. 58-41854.
English Translation of Claims 1, and 2, of JP No. 62-14846.
English Language Abstract of JP No. 52-4515.
An English Translation of a Pertinent Portion of Japanese Publication No. 51 116809.

Primary Examiner—Alan W. Cannon
Attorney, Agent, or Firm—Sandler, Greenblum & Bernstein

[57] ABSTRACT

Ceramic composite comprising a porous ceramic body having directly fitted thereon a dense ceramic body, the composite is produced by a process which comprises the steps of: separately producing the porous ceramic body and the dense ceramic body, inserting a projecting portion of the dense body into a bore portion of the porous body, and simultaneously sintering both the dense and porous bodies at a sintering temperature. The ceramic composite has excellent properties such as heat resistance, resistance to thermal cycle, water resistance and in vivo compatibility, and therefore is particularly useful as an implant material such as an artificial tooth root, an artificial bone and a percutaneous device.

6 Claims, 4 Drawing Sheets

CERAMICS COMPOSITES

BACKGROUND OF THE INVENTION

1. Field of the Invention

The present invention relates to ceramic composites or composite ceramic bodies which are particularly suitable as implants, such as artificial tooth roots, artificial bones, percutaneous devices, etc. The present invention also relates to a process for the production of said ceramic composites.

2. Description of Related Art

Currently, a wide variety of ceramic materials, such as calcium phosphate hydroxyapatite, alumina, and zirconia ceramic materials have been predominantly utilized as implant materials, especially for artificial tooth roots and bones.

These ceramic materials can be produced, by drying a ceramic slurry which is produced by a wet process. After drying, the dried ceramic slurry is pulverized to make a ceramic powder which ceramic powder is then molded to any desired shape. Molding is carried out by a conventional method, such as pressure molding and casting molding. The molded products are subsequently dried and calcined or sintered. Alternatively, the ceramic materials can be produced from powdered ceramics synthesized in a dry process. The powdered ceramics, without further treatment, are molded in a conventional manner to a predetermined shape, and calcined. The ceramic materials resulting from these processes generally have a dense structure.

On the other hand, ceramic materials with a porous structure are also produced. These porous ceramic material can be produced, by adding a foaming agent to a slurry of powdered ceramics and foaming the mixture, or by mixing powdered ceramics with a thermally decomposable organic substance. After molding of the mixture into a predetermined shape, the molded products are dried and calcined.

For use as implant materials, dense ceramics are suited because they have satisfactory strengths. However, due to less permeability to humor or body fluids such as blood and the like, the dense ceramics suffer from the problem that, when implanted in a patient's body, they do not adequately bond to the surrounding tissue of the implantation site. In other words, the dense ceramics do not provide enough of an inductive effect. This inductive effect, which refers to the formation of new osseous cells around the implant, is essential for attaining a good bond of the implant material to the surrounding tissue.

Insofar as the inductive effect is concerned, porous ceramics provide satisfactory results due to the passage of, humor, such as blood, through pores of the porous ceramics. As a result of this permeation of the humor, new osseous cells are easily produced in the area surrounding the implantation site, i.e., a good inductive effect is induced at the site. However, these ceramics do not have enough strength to be used as an implant material because of the porous structure thereof.

Therefore, an improved ceramic body which shows the advantageous properties of both dense and porous ceramics, namely, high strength and a good inductive effect, respectively, has been sought in this field.

Heretofore, to obtain a ceramic body having the advantageous properties associated with both dense and porous ceramics, various attempts, including the combined use of dense ceramics and porous ceramics, have been made. A typical method for producing a combined ceramic utilizes a bonding between the dense ceramic and the porous ceramic. This bonding has been attained by using different methods. For example these methods includes use of an adhesive, formation of an interlayer between the two ceramic bodies, and coating of a ceramic material or body with another ceramic material.

The ceramic composites produced according to said bonding methods have disadvantages that must to be solved. Since the presence of an adhesive layer or interlayer which has different properties from the ceramics used is essential to the first two methods, the resulting ceramic composites tend to have reduced safety to the human body and a reduced inductive effect. Further, the coating method has a drawback that the resultant coating of the ceramic material on the ceramic body is thin and therefore uses of the ceramics composites are severly restricted to. Furthermore, all of said bonding methods have drawbacks that the bonding strength obtained is not sufficiently high, and the bonding site therefore exhibits a reduced strength.

SUMMARY OF THE INVENTION

An object of the present invention is to provide an improved ceramic composite comprising of a porous ceramic body and a dense ceramic body, which can be produced in a simple manner, does not have a layer in an interfacial portion of the composite having different properties from the ceramic, and achieves a high bonding strength between said porous body and said dense body.

Another object of the present invention is to provide a process for the production of said ceramic composite, which is simple, can be carried out with high reproducibility and reliability, and without the drawbacks of the prior art processes described above.

According to the present invention, there is provided a ceramic composite which comprises of a porous ceramic body having directly fitted thereon a dense body. The fitting of the dense ceramic body to the porous body is provided by a bore portion of said porous body into which a projecting portion of said dense body having the corresponding shape is inserted, and said bore portion and said projecting portion are then firmly bonded based on difference of shrinkage between said porous body and said dense body at a sintering or calcination temperature.

According to the present invention, there is also provided a process for the production of a ceramic composite comprising bonded bodies of porous ceramic and dense ceramic, which comprises the steps of:

separately producing, by molding powders of starting ceramic material porous and dense ceramic bodies having a predetermined configuration, inserting at least a portion of said dense ceramic body into a bore portion formed in said porous body, and simultaneously sintering both said dense and porous bodies at an appropriate sintering or calcining temperature, while maintaining the fitted condition of said bodies, so that a difference of shrinkage between said bodies at the sintering temperature will cause enough compression of said inserted part of said dense body with said bore portion of said porous body to firmly and directly bond said dense body to said porous body.

As can be appreciated from the above description, the ceramic composites of the present invention are produced by a simple process which comprises inserting at least a portion of a dense ceramic body into a bore portion of a porous ceramic body, and simultaneously sintering the resulting fitted article of said dense and porous bodies. During sintering, because the higher shrinkage rate or percentage of shrinkage of the porous body compared to the dense body, the dense body is strongly compressed around the bore portion of said porous body whereby the intended ceramic composites consisting of the porous body having directly and firmly fitted thereon the dense body are produced. The production process of the present invention requires only a few steps, and is very simple compared with the prior art processes.

The ceramic composites of the present invention passes show excellent mechanical strengths. In particular, these ceramic composites have a very high bonding strength at the interfacial area between the dense body and the porous body so that the composites are not destroyed even if a diamond disc cutter is used for cutting purposes. This is because the composites do not have an heterogeneous interlayer bonding said dense body and said porous body to form an integral article instead, according to the present invention, the dense body and the porous body are directly bonded by a tight-fitting bond. In addition to the excellent mechanical strength described above, the ceramic composites of the present invention show other superior properties, such as heat resistance, resistance to thermal cycle, water resistance and compatibility with the human body. Thus, they can be advantageously used as implants, such as artificial tooth roots, artificial bones and percutaneous devices.

DESCRIPTION OF THE PREFERRED EMBODIMENTS

Figure 1:
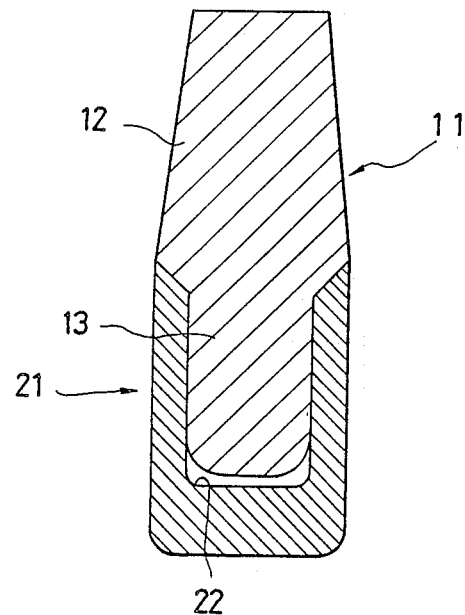
FIG. 1 is a cross-sectional view of the ceramic composite showing a preferred embodiment of the present invention.

In the practice of the present invention, various ceramic materials can be used as the starting ceramics materials. Usable ceramics include calcium phosphate-series or-based ceramics, hydroxyapatite, alumina, zirconia and other types of ceramic. For use of the resulting ceramics composites as biomaterials, calcium phosphate ceramics are particularly suited since they have good in vivo compatibility.

These ceramics can be obtained in a conventional manner, such as a wet synthesis process or a dry synthesis process, from the selected raw materials. For example, when the wet synthesis process is used, the slurry-like ceramics obtained can be dried and ground to form ceramic powders. When the dry synthesis process is utilized, the obtained ceramic powders are in a dry state and can be utilized in the subsequent production of the dense and porous bodies without additional treatments.

According to the present invention, the thus obtained ceramic powders are molded into a dense ceramic body having a predetermined configuration or shape. Molding of this dense body can be performed, for example, by pressure molding methods using a mold press, a rubber press or other means, or by cast molding methods in which a mixture of the ceramic powders with water and a binder such as organic resins and the like is casted. Also, after completion of molding, the molded products may be calcined at an appropriate temperature before the subsequent insertion step, if desired.

Separately, the ceramic powders obtained in accordance with the above-described methods are molded into a porous ceramic body having a predetermined configuration or shape. For example, the porous ceramic body can be produced by foaming a slurry of the ceramic powders or by mixing the ceramic powders with a thermally decomposable organic substance. The foamed slurry or the mixture is then molded to the predetermined configuration, and calcined. Suitable foaming agents that can be added to the slurry of the ceramic powders include any substances capable of causing formation of foams or cells in said slurry, for example, hydrogen peroxide, egg albumen or the like. Suitable thermally decomposable organic substances include any organic materials capable of being decomposed and volatilized upon calcination, for example, beads of organic resins, organic fibers or the like. Using these foaming agents or organic substances, a foamed slurry of the ceramics powders or a mixture of the ceramics powders with the organic substances is prepared, molded by using a manner such as cast molding, and finally calcined. A porous body of ceramics is thus obtained.

The dense ceramic body and the porous ceramic body may each be constructed from the same ceramics, from homogeneous ceramics or from different ceramics. These bodies are preferably made from the same or homogeneous ceramics. The term "homogeneous" used herein is intended to mean that both ceramic bodies have similar natures and exhibit good compatibility when bonded with each other. When different ceramics are used, the bonding strength of the resulting ceramic composites relies upon only an effect of the tight fitting bond based on the shrinkage of the porous body during sintering. However, when the same ceramic or homogeneous ceramics are used in the production of both of the dense and porous bodies, the increased bonding strength of the ceramic composites relies upon the tight-fitting bond based on shrinkage as well as an effect of the sintering at the bonding interface. Namely, when employing the same ceramic or homogeneous ceramics, an increased bonding strength can be obtained.

According to the production process of the present invention, a bore or cavity is formed in a selected position in the porous ceramic body, and at least a part, preferably a projecting part, of the dense ceramic body is inserted into said bore of the porous ceramic body. The bore of said porous body can be produced by various techniques. For example, the bore can be formed at the same time that said porous body is as molded or, by mechanical fabrication, such as cutting, after production of the porous body. Similarly, the projecting part of said dense body, that is to be inserted into said bore of the porous body, can be produced at the same time with the molding of the dense body or at a selected stage after the molding of the dense body. The projecting part should have a shape corresponding to that of the bore of the porous body so that the projecting part is tightly fitted into said bore.

As previously described, the dense ceramic body is inserted into the bore of the porous ceramics body, and then both bodies are sintered to obtain an integral ceramic composite. In order to obtain a completely integral structure and to ensure that an outer surface of the dense body is in intimate contact with an inner surface of the bore of the porous body, the configuration of the bore and the configuration of the insertion part of the dense body must be exactly determined depending upon factors, such as shrinkage factors, of the ceramics constituting said dense and porous bodies. After insertion and before sintering, said dense body and said porous body are preferably loosely fitted, but after sintering, they are tightly fitted. Further, the configuration of the bore can be widely varied depending upon use of the resulting ceramic composites and other factors. While the configuration of the bore is not limited, it is preferably in the form of round holes, square holes, deep-bored holes, through-holes etc. Similarly, the projecting or insertion part of said dense body may have any desired configuration, such as being in the shape of a cylindrical rod, a square rod, a plate, etc. However, the configuration of the projecting or insertion portion depends on the configuration of the bore of the porous body that is used in combination with this dense body. Of course, it is also possible to determine the configuration of said bore depending upon said projecting part.

In addition, the size or dimension of the bore of the porous body and the size of the projecting part of said dense body must each be determined in a range of sizes that no crack due to inappropriate sizes is produced in said porous body and/or said dense body when both bodies are simultaneously sintered. For instance, excessive shrinkage of the bore portion due to an unacceptably increased size thereof will cause crack failures in the projecting part of the dense body, since said part is subjected to excessive compression. To avoid these crack failures, it is contemplated to select the sizes of said bore and projecting part in such manner that a gap is created between the porous body and the dense body, when said dense body is introduced into the bore of said porous body. The size of this gap may be varied widely depending on the bore size, the particular ceramics, the sintering temperature and other factors. In other words, it is necessary to suitably determine this size of gap for each case.

After the insertion of the dense body into the bore of the porous body has been completed, both bodies are simultaneously sintered at an elevated temperature. During this sintering step, the dense body and the porous body start shrinkage thereof at different rates of shrinkage, since the shrinking factor of said porous body is higher than that of said dense body. As an example, when hydroxyapatite is used as the starting ceramic material for producing the dense and porous bodies and both bodies are sintered under the same conditions, i.e., sintering temperature of 1200° C., the dense body exhibits a shrinkage factor of about 80.4%, while the porous body exhibits a shrinkage factor of about 66.2%. Also, the sintered porous body exhibits a porosity of about 35.6%.

Sintering can be carried out in any sintering device which is generally used in this field, for example, the sintering device can be an electric oven or a furnace. The sintering temperature applied is preferably a temperature slightly higher than the temperature which is generally applied when the selected ceramics are sintered. For example, for calcium phosphate ceramics, the sintering temperature is preferably about 1,000° C., and more preferably about 1200° C. For zirconia ceramics, the sintering temperature is preferably about 1600° C.

The present invention will be further described with reference to typical working examples of the present invention. It should be noted that these examples do not restrict the scope of the present invention.

EXAMPLE 1

A slurry of hydroxyapatite was prepared by dropping a phosphoric acid into a slurry of calcium hydroxide. This slurry of hydroxyapatite was then granulated on a spray dryer, and calcined at 700° C. Powders of hydroxyapatite were obtained.

Figure 2A:
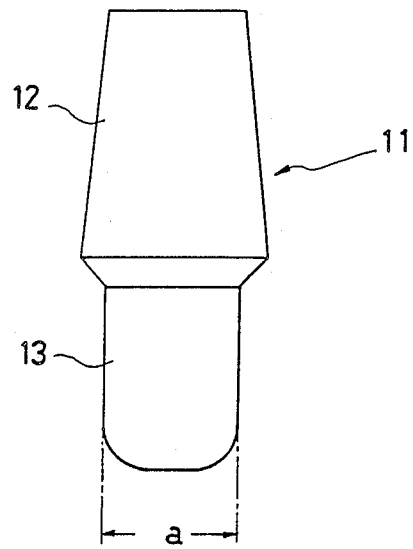
FIG. 2a is a front view of the dense ceramic body used in the production of the ceramic composite of FIG. 1.

To produce a dense body of hydroxyapatite, the powders of hydroxyapatite prepared in the previous step were subjected to a monoaxial pressure molding process, and the molded product was hydrostatically press-molded under a hydrostatic pressure of 2,000 kg/cm$^2$. The molded product was then machined in a NC (numerical controlled) cutting device to obtain a dense body of hydroxyapatite which is shown in FIG. 2a. As illustrated, the dense body of hydroxyapatite 11 comprises a tapered head portion 12 having attached to an end portion thereof a post 13.

Figure 2B:
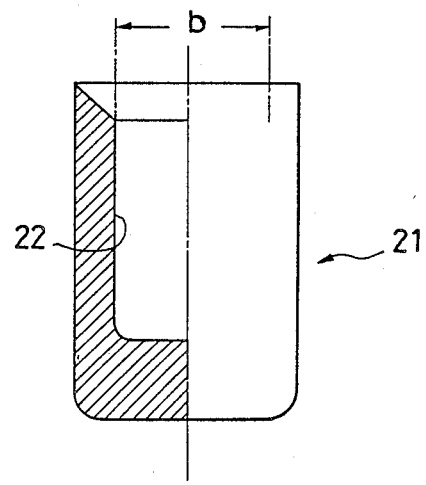
FIG. 2b is a front view, including a cross-sectional view of the left half portion, of the porous ceramic body used in the production of the ceramic composite of FIG. 1.

Separately, the same powders of hydroxyapatite prepared in the previous step were mixed with an aqueous solution of hydrogen peroxide to prepare a foamed slurry of hydroxyapatite. Thereafter, the foamed slurry was dried and calcined to obtain a porous body of hydroxyapatite. The porous body was then machined in a NC cutting device. The resultant porous body of hydroxyapatite is shown in FIG. 2b. As appreciated from this drawing, the porous body of hydroxyapatite 21, as a whole, is in the form of a hollow cylinder with a closed bottom portion. A bore or cavity 22 is positioned in a central portion of the porous body 21.

Next, the post 13 of the dense body 11 was inserted into the bore 22 of the porous body 21, and both bodies 11 and 21 were simultaneously sintered at 1200° C., while maintaining the bodies in a combined condition. A hydroxyapatite composite consisting of the dense hydroxyapatite body and the porous hydroxyapatite body was thus obtained (see FIG. 1).

In this example, experiments were repeated by varying a diameter "a" of the post 13 of the dense body 11, while retaining an inner diameter "b" of the bore 22 of the porous body 21 at 6 mm. The results indicated that sintering was made at an interface of the bodies 11 and 21 when the diameter "a" applied is within the range of 5.0 and 5.9 mm, and that no crack was produced in the porous body 21 when the diameter "a" was 5.0 to 5.6 mm was applied.

Figure 4:
FIG. 4 is an electron microphotograph (magnification×2,000) of the cross-sectional surface of the ceramic composite as is FIG. 3.
Figure 3:
FIG. 3 is an electron microphotograph (magnification×30) of the cross-sectional surface of the ceramic composite of FIG. 1 showing the state of the bonding interface of said composite.

The thus obtained hydroxyapatite composite is photographically shown in FIG. 3, i.e. electron microphotograph (magnification×30) of the bonding interface (cross-sectional surface) of the composite. Also, a more magnified photograph of the bonding interface of the same composite is shown in FIG. 4 in which magnification is ×2,000. These photographs clearly demonstrate that satisfactory sintering was attained at an interfacial portion between the dense body 11 and the porous body 21.

The hydroxyapatite composites of this example are intended to be used as an artificial tooth root. These composites will provide a noticeable increased adhesion to natural bones compared with the prior art artificial root consisting essentially of a dense hydroxyapatite, when they are embedded in said bones, since the composites of the present invention have a base portion covered with porous body 21. Further, it is expected that porous body 21, when utilized as an implant, will become is more strengthened than the inner portion, i.e., dense body 11, because the porous body is changed to a more dense state under the influence of the natural bones.

EXAMPLE 2

Figure 5:
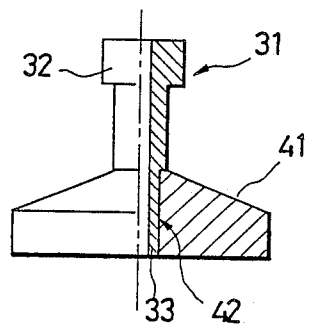
FIG. 5 is a cross-sectional view of the ceramic composite showing another preferred embodiment of the present invention.

A dense body of alumina was produced in the procedure similar to that of Example 1 except that the hydroxyapatite powders were replaced with alumina powders. The pressure-molded product was machined in a NC cutting device to obtain a dense body of alumina which is shown in FIG. 5. As illustrated, the dense body of alumina 31 comprises a head portion 32 having attached to a lower end portion thereof a pin 33.

Separately, a porous body of hydroxyapatite was produced in the procedure similar to that of Example 1. In this example, however, the porous body was NC-machined to a shape shown in FIG. 5. The resultant porous body of hydroxyapatite 41, as appreciated from FIG. 5, has a through-hole 42 in a central portion thereof.

Thereafter, the pin 33 of the dense body 31 was introduced into the through-hole 42 of the porous body 41 and maintained in such combined condition. In the combined condition, the bodies 31 and 41 were sintered at 1400° C. A composite of dense alumina-porous hydroxyapatite, as illustrated in FIG. 5 was obtained.

It was observed that in this alumina-hydroxyapatite composite, the pin 33 of the dense body 31 is tightly compressed with the ring-shaped porous body 41 as a result of shrinkage of the porous body 41.

The alumina-hydroxyapatite composite of this example is intended to be used as a percutaneous element. The percutaneous device is introduced in or under the skin or cutis to periodically conduct a dialysis for renopathy and to periodically determine a concentration of glucose for diabetes, for example, and therefore is not in contact with bones. The reason why this composite is suited to the production of the percutaneous device is that the composite possesses the following two requirements in the field of the percutaneous elements: (1) The elements should be made from dense materials such as apatite or alumina in view of their compatibility with the skin, and (2). The elements should be made from porous materials in view of the need for fixedly maintaining the element during use. The ceramic composites of the present invention can well satisfy these requirements.

I claim:

1. A ceramic composite comprising a porous ceramic body and a dense ceramic body; said dense ceramic body including a projecting portion and said porous ceramic body including a bore portion into which said projecting portion is inserted; said porous ceramic body and said dense ceramic body having a difference of shrinkage factors at a sintering temperature whereby said bore portion and said projecting portion are firmly bonded based on said difference of shrinkage factors between said porous ceramic body and said dense ceramic body.

2. The ceramic composite according to claim 1, wherein said porous ceramic body and said dense ceramic body are made of the same ceramic material.

3. The ceramic composite according to claim 1, wherein said porous ceramic body and said dense ceramic body are made of different ceramic materials.

4. The ceramic composite according to claim 1, wherein the ceramic material of said porous ceramic body and said dense ceramic body is selected from the group consisting of calcium phosphate-series ceramics, alumina, and zirconia.

5. The ceramic composite according to claim 1, wherein said porous ceramic body has a higher shrinkage factor than that of said dense ceramic body.

6. The ceramic composite according to claim 1, wherein the ceramic composite comprises an implant material selected from the group consisting of an artificial tooth root, an artificial bone and a percutaneous element.

* * * * *

UNITED STATES PATENT AND TRADEMARK OFFICE
CERTIFICATE OF CORRECTION

PATENT NO. : 4,969,913
DATED : November 13, 1990
INVENTOR(S) : Satoshi Ojima

It is certified that error appears in the above-indentified patent and that said Letters Patent is hereby corrected as shown below:

On the cover page, Item [54] change "CERAMIC COMPOSITES" to ---CERAMICS COMPOSITES AND PROCESS FOR THEIR PRODUCTION---.
On the cover page, [57], at line 2 under ABSTRACT, change "body, the" to ---body. The---.

Signed and Sealed this

Eighth Day of August, 1995

Attest:

BRUCE LEHMAN

Attesting Officer     Commissioner of Patents and Trademarks